United States Patent [19]
Frank et al.

[11] Patent Number: 5,322,626
[45] Date of Patent: Jun. 21, 1994

[54] DECOUPLED FLOW AND PRESSURE SETPOINTS IN AN EXTRACTION INSTRUMENT USING COMPRESSIBLE FLUIDS

[75] Inventors: Lenore R. Frank; Christopher M. Wurm, both of Landenberg; Paul C. Dryden, West Chester; Steven J. Engel, Kennett Square; Mark A. Nickerson, Landenberg, all of Pa.; Ernest H. Zerenner, Wilmington, Del.

[73] Assignee: Hewlett-Packard Company, Palo Alto, Calif.

[21] Appl. No.: 13,899

[22] Filed: Feb. 5, 1993

Related U.S. Application Data

[60] Division of Ser. No. 804,155, Dec. 6, 1991, Pat. No. 5,240,603, which is a continuation-in-part of Ser. No. 525,964, May 18, 1990, Pat. No. 5,094,741, which is a continuation-in-part of Ser. No. 487,693, Mar. 2, 1990, Pat. No. 5,133,859.

[51] Int. Cl.$^5$ ............................................. B01D 15/08
[52] U.S. Cl. ................................... 210/634; 210/635; 210/656; 210/659; 210/137; 210/143; 210/198.2; 95/19; 95/82; 95/86; 96/103; 203/49; 436/161
[58] Field of Search .................. 202/169, 170; 203/49; 95/19, 82, 86; 96/103; 210/634, 635, 656, 659, 198.2, 137, 143; 422/255, 256; 436/161

[56] References Cited

U.S. PATENT DOCUMENTS

| | | | |
|---|---|---|---|
| 3,046,098 | 7/1962 | Brasseur et al. | 436/178 X |
| 4,168,324 | 9/1979 | Roselius et al. | 426/3112 |
| 4,246,291 | 1/1981 | Prasad et al. | 426/387 |
| 4,247,385 | 1/1981 | Gorin | 208/10 |
| 4,250,331 | 2/1981 | Shimshick | 562/485 |
| 4,283,280 | 8/1981 | Brownlee | 210/198.2 |
| 4,308,200 | 12/1981 | Fremont | 260/110 |
| 4,313,828 | 2/1982 | Brownlee | 210/198.2 |
| 4,341,804 | 7/1982 | Prasad et al. | 426/387 |
| 4,345,976 | 8/1982 | Peter et al. | 203/49 |
| 4,349,415 | 9/1982 | DeFilippi et al. | 203/14 |

(List continued on next page.)

FOREIGN PATENT DOCUMENTS

| | | | |
|---|---|---|---|
| 868151 | 6/1978 | Belgium | 210/198.2 |
| 0065106 | 11/1982 | European Pat. Off. | 210/198.2 |
| 0125690 | 11/1984 | European Pat. Off. | 210/198.2 |
| 0156374 | 3/1985 | European Pat. Off. | 210/198.2 |
| 0171079 | 12/1986 | European Pat. Off. | 210/198.2 |
| 88100485.7 | 1/1988 | European Pat. Off. | 210/198.2 |

(List continued on next page.)

OTHER PUBLICATIONS

Abstract of Japan Patent No. 60291155, *Patent Abstracts of Japan*, vol. 011-378 Dec. 24, 1985, p. 1.

*Primary Examiner*—Ernest G. Therkorn
*Attorney, Agent, or Firm*—Richard E. Schuette

[57] ABSTRACT

Methods and apparatus for extracting sample components from complex matrices using supercritical fluid as the principal extracting solvent are disclosed. The invention takes advantage of the fact that the solvent power of a supercritical fluid is stepwise settable by the parameters of density, modifier concentration, and temperature. Accordingly, methods and apparatus for extracting a component from a sample using fluid flow system having a variable and controllable flow restriction are disclosed. The methods of the present invention comprise the steps of inserting the sample into the sample container section, inputting temperature, pressure, flow rate and extraction time set points. Flow rate is controlled and system pressure regulated by the variable flow restriction. The output stream from the extraction is then expanded through a nozzle and into a trap. In certain embodiments, the trap is filled with chemically active packing material. In other embodiments, a fractionation zone and other analytical instruments are coupled to the apparatus of the present invention. Methods and apparatus for rinsing the extraction instrument and for diluting the extraction fluid are also disclosed. Methods for operating a supercritical fluid extraction systems comprising a pressure and thermal control systems which are programmable to regulate the system to maintain such values within the design specifications during the extraction process.

7 Claims, 8 Drawing Sheets

U.S. PATENT DOCUMENTS

| | | | |
|---|---|---|---|
| 4,354,922 | 10/1982 | Derbyshire et al. | 208/68 |
| 4,363,717 | 12/1982 | Pelrine et al. | 208/108 |
| 4,375,387 | 3/1983 | deFilippi et al. | 202/169 |
| 4,388,171 | 6/1983 | Corcoran et al. | 208/8 LE |
| 4,397,731 | 8/1983 | Warzel | 208/8 LE |
| 4,400,559 | 8/1983 | Bhise | 568/858 |
| 4,406,742 | 9/1983 | Dick | 196/14.52 |
| 4,422,966 | 12/1983 | Amer | 260/97.6 |
| 4,437,938 | 3/1984 | Bhise et al. | 203/14 |
| 4,437,939 | 3/1984 | Bhise et al. | 203/14 |
| 4,438,816 | 3/1984 | Urban et al. | 166/303 |
| 4,447,310 | 5/1984 | Derbyshire et al. | 208/8 LE |
| 4,448,669 | 5/1984 | Scinta | 208/11 LE |
| 4,449,586 | 5/1984 | Urban et al. | 166/303 |
| 4,451,363 | 5/1984 | Brownlee et al. | 210/198.2 |
| 4,451,364 | 5/1984 | Higgins et al. | 260/412.8 |
| 4,457,812 | 7/1984 | Rado | 204/66 |
| 4,457,846 | 7/1984 | Munk | 210/656 |
| 4,474,994 | 10/1984 | Makin | 568/438 |
| 4,478,715 | 10/1984 | Goodnight, Jr. | 210/198.2 |
| 4,493,797 | 1/1985 | Avedesian | 530/507 |
| 4,495,095 | 1/1985 | Lawson et al. | 260/97.7 |
| 4,500,432 | 2/1985 | Poole | 210/659 |
| 4,512,899 | 4/1985 | Goodnight, Jr. | 210/656 |
| 4,547,292 | 10/1985 | Zarchy | 210/634 |
| 4,568,495 | 2/1986 | Frihart | 260/428.5 |
| 4,584,140 | 4/1986 | Blewett et al. | 260/412.8 |
| 4,597,943 | 7/1986 | Sugiyama et al. | 422/70 |
| 4,601,906 | 7/1986 | Shindler | 424/195.1 |
| 4,632,837 | 12/1986 | Schutz et al. | 426/425 |
| 4,816,159 | 3/1989 | Khosah | 210/198.2 |
| 4,840,730 | 6/1989 | Saxena | 210/659 |
| 4,871,453 | 10/1989 | Kumar | 422/70 |
| 4,892,654 | 1/1990 | Nickerson | 210/198.2 |
| 4,913,821 | 4/1990 | Melcher et al. | 426/178 X |
| 4,969,993 | 11/1990 | Nash | 210/198.2 |
| 4,984,602 | 1/1991 | Salto et al. | 137/487.5 |
| 5,004,538 | 4/1991 | Apfel | 210/198.2 |
| 5,009,778 | 4/1991 | Nickerson | 210/198.2 |
| 5,013,443 | 5/1991 | Higashidate | 210/198.2 |
| 5,094,741 | 3/1992 | Frank | 210/659 |
| 5,133,859 | 7/1992 | Frank | 210/659 |
| 5,151,178 | 9/1992 | Nickerson | 210/659 |
| 5,240,603 | 8/1993 | Frank | 210/198.2 |

FOREIGN PATENT DOCUMENTS

| | | | |
|---|---|---|---|
| 2853065 | 6/1980 | Fed. Rep. of Germany . | |
| 2855191 | 6/1980 | Fed. Rep. of Germany . | |
| 3323940A1 | 1/1985 | Fed. Rep. of Germany . | |
| 211580 | 7/1984 | German Democratic Rep. . | |
| 55-85247 | 6/1980 | Japan | 210/198.2 |
| 59-186975 | 10/1984 | Japan | 210/198.2 |
| 60-35057 | 2/1985 | Japan | 210/198.2 |
| 60-58498 | 4/1985 | Japan | 210/198.2 |
| 60-62773 | 4/1985 | Japan | 210/198.2 |
| 60-92397 | 5/1985 | Japan | 210/198.2 |
| 60-105690 | 6/1985 | Japan | 210/198.2 |
| 60-116641 | 6/1985 | Japan | 210/198.2 |
| 60-199891 | 10/1985 | Japan | 210/198.2 |
| 60-229996 | 11/1985 | Japan | 210/198.2 |
| 60-291155 | 12/1985 | Japan | 210/198.2 |
| 61-72096 | 4/1986 | Japan | 210/198.2 |
| 1177219 | 1/1970 | United Kingdom | 210/198.2 |
| 2132223A | 7/1984 | United Kingdom | 210/198.2 |

RINSE

EXTRACT

DECOUPLED FLOW AND PRESSURE SETPOINTS IN AN EXTRACTION INSTRUMENT USING COMPRESSIBLE FLUIDS

CROSS-REFERENCE TO RELATED CASE

This is a divisional of U.S. Ser. No. 07/804,155 Dec. 6, 1991, now U.S. Pat. No. 5,240,603, which is a continuation-in-part of U.S. Ser. No. 525,964 filed May 18, 1990 now U.S. Pat. No. 5,094,741, which is a continuation-in-part of U.S. Ser. No. 487,693 filed Mar. 2, 1990 now U.S. Pat. No. 5,133,859.

FIELD OF THE INVENTION

The present invention relates to methods and apparatus for extracting materials from a substance and, more particularly to supercritical fluid extraction.

BACKGROUND OF THE INVENTION

Supercritical fluids can be used as solvents in extraction instruments, chromatographs and other related instruments. The supercritical region is often defined by all temperatures and pressures above the critical temperature and pressure. The critical temperature is that temperature above which the distinction between gases and liquids disappears; there is one fluid phase for all pressures. No matter how much pressure is applied, a liquid phase cannot be condensed. A supercritical fluid can be defined as a substance at a temperature above its critical temperature, and the critical pressure can be defined as the pressure corresponding to the critical temperature value when the values at which a liquid and gas coexist for a substance are plotted on a pressure-temperature graph. Thus, the absence of the possibility of gas-liquid equilibrium is often used to define a supercritical fluid. Supercritical fluids are a useful hybrid of gases and liquids as we commonly perceive them, possessing gas-like viscosities, liquid-like densities, and diffusivities greater than typical liquid solvents. The liquid-like density of a supercritical fluid imparts a variable liquid-like solvent power which is essentially a linear function of density over significant ranges in density. This allows the solvent power, usually considered a chemical interaction, to be set ("dialed in") simply by adjusting a physical parameter, namely density or pressure. Variable solvent power is most pronounced over densities corresponding to pressures from about 0.8 times the critical pressure to pressures at which the solvent densities become nearly liquid-like.

Another important aspect of supercritical fluids is that compared to typical liquid solvents the supercritical fluid transport properties of viscosity and diffusivity allow enhanced mass transport within complex matrices, such as coal, plant or animal tissue, or packed beds. In other words, supercritical fluids penetrate better and dissolve almost as well as typical liquids. Therefore, supercritical fluids are more efficient to use for extractions of complex matrices.

Even though the solvent power of a supercritical fluid is variable, each supercritical fluid has a maximum solvent power approaching that of the substance as a liquid. Although the solvent power of a liquid is also variable and also essentially a linear function of the density, far larger increases in pressure are necessary to produce significant increases in liquid solvent power. For a typical laboratory liquid solvent such as methanol, the pressure can be lowered to atmospheric and a solution of solvent and solute is stable. Heat must be supplied to drive off solvent for solution concentration or solute drying. If a liquid with a very high vapor pressure at ambient temperatures is used, such as liquid carbon dioxide or ammonia, the solvent is readily evaporated upon solution decompression, leaving a dry, concentrated solute. However, there is a discontinuity in the density along an isotherm corresponding to the lines between coexisting liquid and gaseous phases. Because of the discontinuity in density solvent power essentially is made high or low, e.g., "go" or "no-go", and most of the versatility in solvent power control is lost.

In terms of mass transport properties, diffusivity is an important parameter. Liquid diffusivities cover a large range, some of which (e.g., carbon dioxide and ammonia) are almost the same as those of the supercritical fluid when the liquid is at near critical conditions. In those cases either the liquid or the supercritical fluid would suffice for efficient extraction. However, for commonly used liquids, the diffusivities are lower by a factor of 10 to 100 than for supercritical fluids and therefore these liquids are less efficient in terms of the time required for extraction.

Supercritical solvents are therefore superior in that they (1) allow a large continuous range of solvent powers, thus providing for selective solvation of solutes over that range, (2) provide a means of rapid and complete solvent/solute separation with minimal heat input, and (3) can decrease the time for extraction of complex matrices by a factor of 10 to 100.

Carbon dioxide is the principal extracting fluid used in supercritical fluid extraction systems since it is cheap, innocuous, readily available at high purities, and has a critical temperature of about 31° C. making it useful for thermally labile compounds. Furthermore, it is mutually soluble with many common liquid solvents. It has been found that carbon dioxide has a solvent power similar to that of hexane. However, many applications exist which require greater solvent power, the advantageous properties of supercritical fluids, and mild operating temperatures for thermally labile compounds. Mixtures of carbon dioxide plus modifiers can meet these requirements. As well known to those of ordinary skill, supercritical fluids can be used as solvents in extractions and chromatography; in such applications carbon dioxide is the preferred solvent. Other fluids which have critical points near ambient temperature (25° C.) such as ethane, nitrous oxide, ethylener or sulfur hexafluoride could also function as the base solvent. The capability to utilize these alternatives is preferably not exploited because of the inherent danger and greater expense associated with using these solvents.

Another way to increase the solute solubility in supercritical fluid systems is through temperature control. It has been demonstrated that for some solutes a certain minimum temperature is necessary for appreciable solute solubility in a supercritical fluid, even at maximum densities, so temperature is also a solvent power parameter beyond the simple P-T relationship with density.

The problem encountered in building extraction systems which use compressible fluids at pressures above atmospheric (ambient) is that the pressure of the fluid system is coupled with the mass flow rate of the flowing fluid. This is a result of the use of restrictors having constant geometry to achieve a pressure drop from higher pressures to lower pressures which are normally, but not restricted to ambient or vacuum conditions, so that the only practical way to achieve higher pressures upstream of the restriction is to increase the mass flow rate. Alternatively, to maintain the same mass flow rate at higher pressures, a fixed geometry restrictor of smaller dimensions can be substituted; however, such a substitution requires a physical intervention of some kind. However, in operating these extraction systems it is highly desirable to have the same mass flow rate at all pressures, i.e., with the lower flow rates to achieve-lower pressures, the time to flow a chosen net amount of fluid can be significantly longer than at higher pressures, e.g., hours vs. minutes. Therefore, in a system which can be adjusted to operate sequentially at multiple pressures (e.g., 1100 psi, 1300 psi, 1500 psi, 3000 psi, 6000 psi) at flow rates which provide the same integrated mass of expanded carrier fluid at each pressure setting the time to complete the method can be so long that the method becomes inefficient. This is particularly true in operating supercritical fluid extraction systems, as well as near-critical fluid extraction, which can be more efficient in time than extractions using conventional fluids, due to the transport properties (e.g., viscosity, diffusivity) of critical and near-critical fluids. However, that efficiency is lost when the parameters of pressure and flow cannot be decoupled because of the hardware implementation, e.g., constant geometry flow restrictions.

It is therefore an object of the present invention to decouple the pressure and flow parameters so that they can be set and controlled independently.

In the past, operators of supercritical fluid chromatograph (SFC) and supercritical fluid extractor (SFE) instruments selected pressure and temperature parameters to set the desired density parameter indirectly. Density is usually a more meaningful parameter than pressure in supercritical (and near-critical) systems due to its simple linear relationship to the fluid's solvent power. Often, in any previous implementations of supercritical fluid systems, only pressure and temperature inputs have been allowed; calculating the resultant density or even understanding the pressure/density/temperature relationship has been left to the user, albeit occasionally prompted by abbreviated look-up tables. Therefore, in those cases, controlling the solvency has relied upon the technical sophistication and persistence of the user to apply equations of state appropriately.

The extraction of solids has typically been done manually in conventional laboratory glassware. Laboratory devices which automate the steeping of the sample in a boiling liquid solvent along with the subsequent concentration of the resultant solution are sold commercially as the "Soxtec" by Tecator. This device does not permit fractionation as part of the method; the output is not in autosampler-compatible vessels and samples are boiled at temperatures determined by the boiling points of the extracting solvents, which can be detrimental to thermally labile compounds. Recently, several companies have offered instruments based on using supercritical fluids: Milton Roy, Suprex, CCS, Lee Scientific/Dionex, and Jasco. The implementations by these companies are not exceptionally sophisticated or automated; they require various degrees of manual intervention. In these implementations, the full capability of using supercritical fluids for quantitative extraction is not realized Thus, there exists a long-felt need to design an instrument which could be used to isolate various materials from solid samples using supercritical fluid technology. Either the isolated materials (extract) or the material remaining (raffinate) could be of interest. The process of isolation is referred to as extraction. The need also exists to automate the extraction of solids, since the procedures are typically manually intensive. In the business of preparing samples for analytical instruments, it would be highly desirable to automate sample preparation of raw samples to obtain a form compatible with introduction into typical analytical instruments used in laboratories worldwide. The extraction of solids is often accompanied by other manipulations such as fractionation (e.g., by column chromatography), concentration, solvent exchange, and reconstitution. A method comprised of these generic manipulations may actually consist of many (ranging from several to hundreds) of manual steps. It would therefore be desirable to produce an instrument which replaced the above-mentioned generic manipulations so that the only step required was to present a sample to the extraction instrument and receive fractions of isolated material in vessels compatible with the autosamplers of analytical instruments.

Improvements in the isolation of selected material from solid samples and the automation of the generic manipulations of processes such as extraction, fractionation, concentration, solvent exchange, and reconstitution are clearly desirable goals. It would be desirable and of considerable advantage to use a technique different from the traditional laboratory manipulations known to those of ordinary skill if such a different technique provided superior performance in any of the following areas: quantitation, repeatability and reproducibility, speed, automation, automatability, health hazard reduction, or cost reduction (materials and labor).

Ideally, an extraction instrument would be a stand alone module, that is, a component instrument within an integrated system. In such systems it is also highly desirable to provide robotic accessibility for inputting the sample and retrieving the fraction in an automated fashion. An important aspect of any extraction system therefore lies in its upgradability for automating the sample input (i.e., adding an autosampler for solid samples) and automating the fraction output (i.e., fraction collection with further chemical manipulation and large-scale queuing); an external pump module for blending extraction fluid composition could also be a future addition.

Another improvement in the utility of extraction systems would be the use of standard input and output containers for the sample which is input and the fraction solutions which are output. The instrument would accordingly be provided with a multiple sized extraction chamber which accepts the solid samples.

An improved extraction instrument would also incorporate an automated "method", with a, method being defined as that sequence of manipulations associated with any one sample. Examples include, but are not limited to, valve actuation, thermal zone setpoint changes, extraction fluid solvent selection, reconstitution solvent selection, flow path selection, fraction output destination, density/pressure setpoint changes, flow rate setpoint changes. Such an automated extraction instrument would also provide automatic selectable output destinations within a method, and from method to method; automatic selectable inputted extraction fluid composition within a method and from method to method; and automatic selectable rinse solvents for the solvent exchange/reconstitution emulation processes within a method and from method to method.

SUMMARY OF THE INVENTION

The present invention provides a sample preparation device which extracts sample components from complex matrices using supercritical carbon dioxide as the principal extracting solvent and presents the resulting extract in a user-chosen sample collection vessel (autosampler vial, bulk vessel, cuvette, etc.) with the autosampler vial being directly compatible with automatic injection systems of other analytical instruments (e.g., liquid chromatograph, gas chromatograph, supercritical fluid chromatograph). The present invention replaces traditional preparative procedures such as solvent extraction, Soxhlet extraction, liquid/liquid extraction, concentration, and evaporation. With the solvent power stepwise settable by the parameters of density, modifier concentration, and temperature, the supercritical fluid extractor can mimic column chromatography sample fractionation in some applications.

Accordingly, methods of extracting a component from a sample using fluid flow system apparatus comprising control apparatus, at least one element having a variable and controllable flow restriction and a sample container section are disclosed. The methods of the present invention comprise the steps of inserting the sample into the sample container section, inputting temperature, pressure or density, flow rate and extraction time setpoints into a control apparatus and providing pressurized fluid. By directing the fluid to a pump which injects the fluid into the flow system apparatus at the input flow rate setpoint the extraction process is initiated. The system pressure is sensed as fluid is pumped into the system and the variable flow restriction is regulated to achieve and to maintain the setpoint pressure. Extraction is accomplished by directing fluid through the sample at the setpoint flow rate and directing a fluid mixture leaving the sample container section to an expansion nozzle section. Preferably, the methods of the present invention include maintaining the controlled setpoints of flow, pressure, and temperatures until the input extraction time is achieved. In certain embodiments, the step of inputting the setpoints is repeated to generate a method of extraction which varies those parameters in the order prescribed. The methods of the present invention contemplates opening and closing the orifice in order to control the variable flow restriction, or closing the orifice until setpoint pressure is achieved and controlling the restriction of the orifice to maintain the setpoint pressure.

The present invention also discloses apparatus for the extraction of components from a sample. Preferably, a pump for maintaining a liquefied gas, comprising a pump motor and a pump motor speed control are provided along with means for regulating the pressure of the output of the pump to a setpoint pressure. The flow rate of the fluid is thus controlled by the pump. Pressurized fluid is directed to an extraction section means for retaining a sample by a flow system. The apparatus also comprises a nozzle having a variable orifice that controls the pressure and a pressure transducer for providing a pressure signal connected to a regulator feedback loop from the pressure transducer. In certain embodiments of the present invention, the pressure transducer provides a signal to the pump motor speed control. The pressure drop across the nozzle permits the recovery of dissolved material precipitating from the expanding fluid, while the parameters of flow and pressure are decoupled. In one alternate embodiment the regulator feedback loop controls the speed of the pump to maintain the pressure of the fluid at a predetermined value, and the nozzle having a variable orifice is set to create a restriction which limits the mass flow rate of the pressurized fluid to a predetermined value. However, in a preferred alternate embodiment, the pump comprises a metering pump for providing a controlled mass flow rate, and the nozzle having a variable orifice is set to create a restriction which maintains the pressure of the pressured fluid to a predetermined value.

Thus, several preferred embodiments of apparatus for the extraction of components from a sample made in accordance with the present invention are disclosed. The system described comprises one or more sources of solvent fluid and one or more extraction solvent fluid input ports connected to a high pressure pump. A pressure transducer measures the pressure of the fluid delivered by the high pressure pump. An extraction chamber flow system is preferably provided comprising an extraction chamber for retaining the sample in the flow stream of the fluid and a sample input module for containing the sample in the extraction chamber. A bypass flow system may also be provided in certain embodiments to route fluid flow around the extraction chamber section. These flow systems are joined by a means for merging the bypass flow system and extraction chamber flow systems. In order to isolate the extracted component, the present invention utilizes a sample collection means for separating the extracting solvent fluid from components from the sample, comprising at least one nozzle and trap subassembly. A flow transducer may also be incorporated, as well as at least one sample collection vessel. In this embodiment of the apparatus of the present invention, pressurized liquid is flowed through the sample under independently predetermined and controlled conditions of flow and pressure, dissolves one or more selected components from the sample, and the components are collected by the sample collection apparatus. Certain embodiments use two pressure transducers; one for use as part of the pressure control loop and placed optimally in the fluid system for stable control operation. The second transducer is used to sense fluid pressure for diagnostic troubleshooting operations and safety electronic interlocks. Numerous variations and additions to the basic apparatus described are set forth in detail below.

Finally, the present invention also discloses methods for operating a supercritical fluid extraction system comprising pressure and thermal control systems which are programmable by a user to predetermined values and regulate the system to maintain such values. First, the user inputs the operating fluid setpoint density and zone temperatures and the system rounds the setpoint density to a value which is distinguishable as a setpoint at the given region of the equation of state for the fluid. Next, the system calculates the operating pressure corresponding to the setpoint density using known relationships between these variables. The user is notified if the values of density and temperature result in pressures outside the operating region of the instrument and the operating pressure and other values are then displayed. Finally, the system transmits values to the pressure and temperature control systems maintaining the setpoint density within the design specifications during the extraction process.

The present invention may also be adapted in certain embodiments to provide methods and apparatus whereby the instrument, in particular the nozzle, may be rinsed with solvent in order to prevent occlusion or other problems associated with the accumulation of particulate matter. Also, certain embodiments of the present invention may comprise additional apparatus for selectively diluting the stream of extraction fluid after it has exited the extraction chamber.

BRIEF DESCRIPTION OF THE DRAWINGS

FIGS. 2C-2D illustrate alternate embodiments of the variable static restrictor shown in FIG. 2B.

DETAILED DESCRIPTION OF THE PREFERRED EMBODIMENTS

In accordance with a first aspect of the present invention, flow and pressure setpoints may be decoupled. A user initiates a method for supercritical fluid extraction in accordance with the present invention by inserting the sample in the flow system and inputting temperature control setpoints and a control pressure or a density setpoint. If the latter is chosen the control pressure must be calculated using the density setpoint entry. The operator then inputs a control flow rate, lengths of time for static and dynamic extraction steps—which determine how long the sample will remain or "steep" in the stagnant extracting fluid and then how long the extracting fluid will flow through the sample—along with system parameters. The method of the present invention then repeats the parameter setpoint selection for all steps to generate a complete extraction cycle which varies those parameters in the order prescribed by the user. By issuing a "Start" command, the instrument then pursues the following steps: (1) withdrawing fluid, either as a gaseous layer or a liquid layer, from standard gas cylinders with their contents at pressures above the ambient or atmospheric pressure; (2) directing the withdrawn fluid to a pump which is electronically controlled to deliver fluid to the rest of the extraction system at the flow rate selected; (3) sensing the system pressure as fluid is injected into the system; (4) controlling a nozzle orifice size to achieve setpoint pressure during the injection of fluid into a closed system; (5) initiating time measurement in order to compare to setpoint extraction times; (6) controlling the nozzle orifice to an appropriate degree of restriction thereby maintaining a setpoint pressure and temperature with no flow through the sample for the equilibration time prescribed by the user once it is achieved, fluid injection into the system continues at the setpoint flow rate, also known as dynamic extraction. Fluid is then directed through the flow path selected through the sample container section. The system then directs the fluid mixture leaving the sample container section to the expansion nozzle section, and continues to maintain all controlled setpoints of flow, pressure, and temperatures until the dynamic extraction time input has elapsed.

Figure 1:
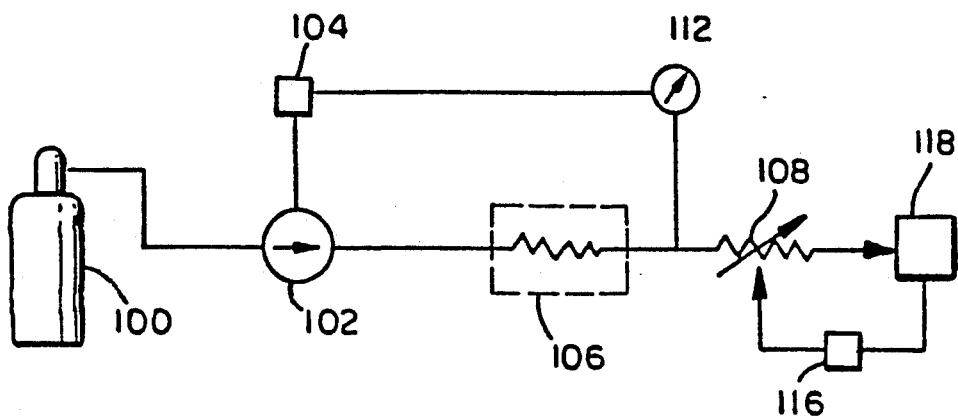
FIG. 1 is a simplified schematic representation of an extraction system made in accordance with the present invention.

Referring now to FIG. 1, an embodiment of the extraction system of the present invention using supercritical and near-critical fluids is shown. The system first pressurizes carbon dioxide or other fluids or fluid mixtures from gas cylinders 100 using a pump 102 which has a regulator 104 which controls the setpoint pressure. The flow system directs the pressurized fluid to an extraction section 106 holding a sample which contains components to be isolated. The system then directs the fluid solution to a nozzle 108 where it is depressurized to lower (e.g., atmospheric) pressures. In the embodiment shown, the nozzle 108 has a variable orifice set to create a restriction which limits the mass flow rate. In a most preferred embodiment, the variable orifice is created using an axially-driven valve such as that disclosed in U.S. Pat. No. 5,009,778—Nickerson et al. which is assigned to the assignee of the present invention and incorporated herein by reference. in such an embodiment, steps (4) and (6) set forth immediately above would entail an active control of the orifice. Alternatively, as pointed out above, a series of static orifices can be provided and interchanged to provide discrete pressure levels (e.g., 1100 psi, 1300 psi, 1500 psi, 3000 psi, 6000 psi) at flow rates that provide the same integrated mass of expanded carrier fluid at each pressure setting. Such a system is generally useful in an extraction instrument, and such "step wise variable" orifices are nevertheless also useful in certain embodiments of the present invention. With such a system, the manipulation of various valves is required to achieve static extraction conditions. Alternatively, in a system as depicted in FIG. 1 having a manually variable orifice restrictor, the user must function to sense the flow rate and adjust the orifice.

In the embodiment shown in FIG. 1 achieving setpoint pressure is preferably accomplished by regulating the speed of the pump 102 using the regulator 104. The regulator 104 is part of a feedback loop from a pressure transducer 112 which provides a signal to the pump motor speed control 104 to gain operating stability at the selected pressure setpoint. A flow transducer 118 is provided as part of a control loop 116 which regulates the physical restriction of the variable orifice of the nozzle to control the setpoint flow rate in those embodiments having an electronically variable orifice restrictor. Both decoupled parameters are therefore set independently.

Figure 2:
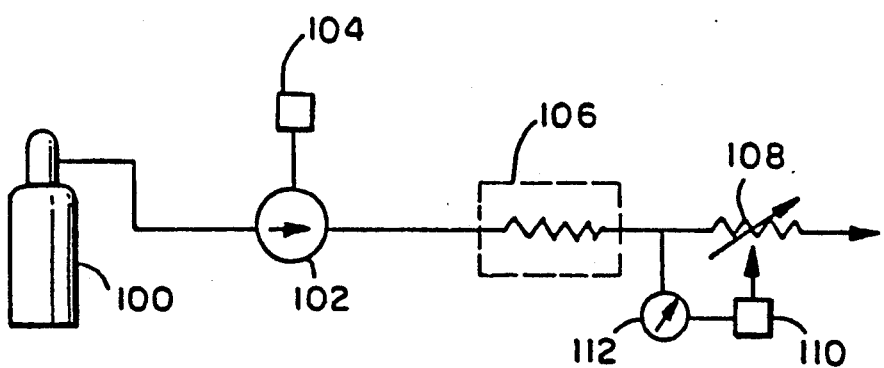
FIG. 2 depicts another simplified schematic representation of another embodiment of the present invention.

In another preferred embodiment of the present invention depicted in FIG. 2, fluid is pumped by a metering pump 102 at a given flow rate as provided by the metering control electronics 204 to supply the rest of the flow system with a controlled mass flow rate. Again, fluid flows through the sample in an extraction section 106 which is immersed in the flow path, dissolves material from the sample, and goes through a pressure drop at the nozzle 108. The nozzle 108 functions as a restrictor causing the pressure drop in the high pressure solution to recover dissolved material precipitating from the expanding extraction fluid, as well as a back pressure regulator for the pressurized system. In those embodiments having a variable orifice, a control loop 110 using a signal from a pressure transducer 112 controls the physical restriction in the nozzle 108 to maintain a setpoint pressure for the whole range of mass flow rates metered out by the pumping system ranging from no flow to about 4 g/min. As explained above and understood by those of ordinary skill, a variable orifice nozzle 108 may be implemented in a variety of ways; for example, a modified needle valve can be constructed, with particular attention paid to expansion region design or in accordance with the valve disclosed in U.S. Pat. No. 5,009,778 referenced above. In another embodiment, a range of static orifices are provided and are discretely chosen to regulate the system pressure while accommodating the selected mass flow rates. Alternatively, in a system such as that depicted in FIG. 2 and having a manually variable orifice restrictor, the user must function to sense the pressure and adjust the orifice.

Figure 2A:
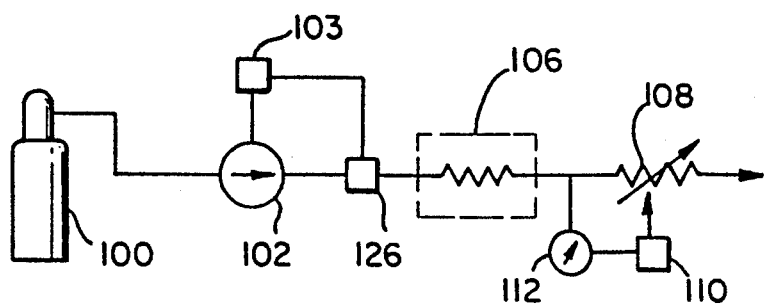
FIG. 2A illustrates an alternate embodiment of the system shown in FIG. 2.

A modification to the system shown in FIG. 2 is depicted in FIG. 2A. In this embodiment, a flow transducer 26 is added downstream from the pump 102. The flow transducer 126 provides a feedback flow signal to the pump controller 103 and permits the system to monitor the flow rate on the high pressure side of the pump. Although the flow transducer 126 is illustrated in a position upstream from the extraction section 106, it could also be positioned downstream from the extraction section 106. The flow transducer 118 can also be placed even farther downstream, beyond the nozzle, in a configuration as shown in FIG. 1, but employing a flow rate control loop controlling the pump.

The variable orifice embodiments of the present invention that are disclosed herein for systems as depicted in FIGS. 1, 2 and 2A would ideally provide a near-continuum of both setpoint pressures and flows. As outlined above, the alternative of providing and interchanging a series of static orifices provides only some number of discrete pressure levels at similar flow rates. Also, the precision and accuracy of the control of the parameters of flow and pressure with static orifices is far more difficult to control adequately. For example, tolerances in fabricating such static orifice restrictors must be held very tightly—particularly on those dimensions contributing to cross sectional areas since they contribute as squared terms. In the operation of such a system using static orifices, any occlusion of the flow passage within it—by clusters of expanding mobile phase, by precipitating clusters of heretofore dissolved solute(s), or by insoluble particles generated by wear of the apparatus or from the samples being extracted—will alter the mass flow through the restrictor, thereby deviating from setpoint values of pressure and/or flow rate. The electronic control of the relative proximity of the variable orifice restrictor allows real-time modification of the restrictor via the control loop so that setpoint values are more robustly maintained throughout the operation of the system for ranges of conditions and sample types. With embodiments using static orifices or manually variable orifices, periodic manual intervention is necessary to achieve and maintain setpoints as such systems operate.

Figure 2B:
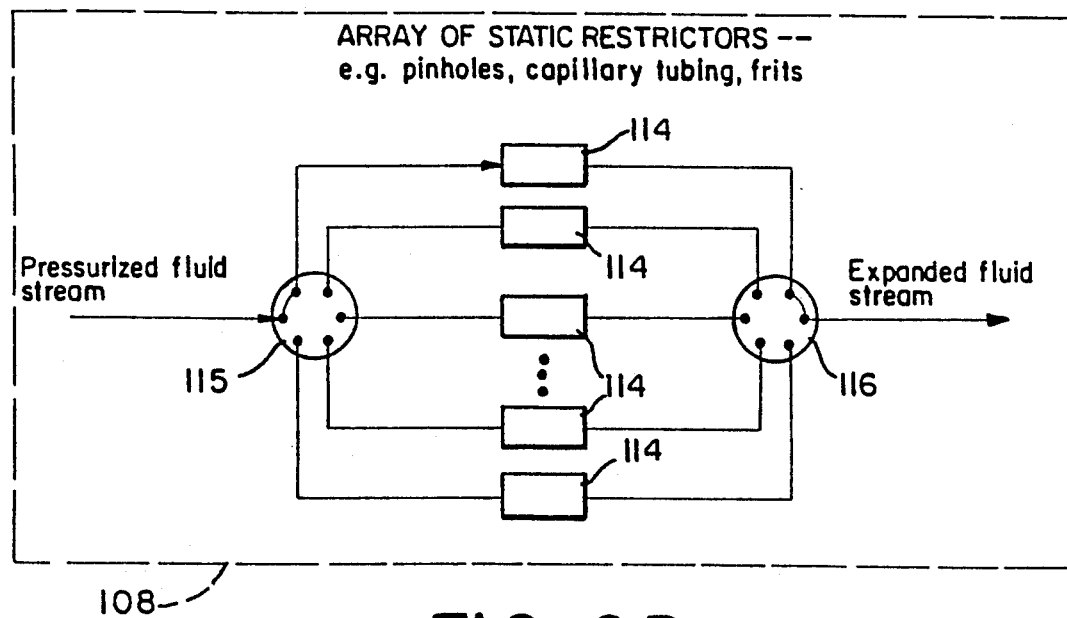
FIG. 2B is a schematic illustration of an implementation of a variable static restrictor for use in the present invention.

Thus, referring now to FIG. 2B, there is illustrated an embodiment of a variable restrictor 108 as discussed above with reference to FIGS. 1-2 and 2A that comprises a plurality of static restrictors 114 disposed between and connected to two multiple port valves 115, 116 that selectively connect the pressurized fluid stream to one of the static restrictors 114. The array of static restrictors 114 comprises restrictors that have different orifice openings, thereby permitting a particular mass flow rate and/or pressure to be achieved. As noted above, depending upon the apparatus in which this variable restrictor 108 is incorporated, step-wise independent selection of pressure and flow points may be accomplished by varying the degree of restriction. As will be realized by those of ordinary skill, the static restrictors 114 are comprised of pinhole fittings, capillary tubing, frits or any other structure having an appropriate restriction that can be connected to the apparatus being controlled. By using the appropriate combination of hydraulic conduits, valves 115,116 and restrictors 114 and implementing the appropriate logic algorithms in the control system, the selection of independent pressure and flow setpoints can be automated With no manual intervention by the user.

As shown in FIG. 2C, another possible embodiment of a variable restrictor 108 that incorporates a plurality of static restrictors 114 having varying degrees of restriction can be constructed within a single flow path. Unlike the embodiment shown in FIG. 2B, the embodiment of FIG. 2C requires manual intervention and an interruption of the pressurized fluid flow in order to change the degree of restriction. The static restrictor 114 is simply chosen from a group of static restrictors 114 designed to be interchangeably connected into the pressurized fluid stream as shown. This embodiment of the variable restrictor 108 is therefore akin to providing a manually adjusted needle valve, however, when using a needle valve, the discrete plurality of static restrictors 114 would be unnecessary. Such an embodiment will generally require a different sequence of operation, as the flow stream must be interrupted each time the degree of restriction is varied.

It should be noted that in both the embodiment depicted in FIG. 2B as well as the embodiment depicted in FIG. 2C, the flow rates among several of the plurality of restrictors 114 can be the same such that only the pressure designated as the control pressures are different. Conversely, the flow rate setpoint values may differ, and the control pressure setpoint values can be the same between several of the restrictors 114. The provision of step-wise selection of the restrictor components to a large degree permits the user to independently choose the combinations of flow and pressure, thereby achieving a degree of decoupling of those parameters.

Finally, another embodiment of a variable restrictor is illustrated in FIG. 2D. In this embodiment, the static restrictors 114 are manually varied, as discussed above with reference to FIG. 2C. However, by providing two port valves 117,118 and two flow streams, the flow of pressurized fluid does not have to be interrupted each time a restrictor 114 is changed. As with the embodiment shown in FIG. 2B, this embodiment permits on-line step-wise independent selection of pressure and flow setpoints. The provision of two flow paths and appropriate valves 117,118 permits the overlap of restrictor installation time with instrument operation time, i.e., uninterrupted flow.

When using supercritical fluids the parameter of density, which is a function of pressure and temperature, is directly related to solvent power (solvency) of the fluid; therefore, solvent power is adjustable and selectable by setting and regulating 2 of the 3 parameters. Since pressure transducers are common and density transducers at the operating conditions of typical extraction devices are not, it is preferable (but not absolutely necessary) to select the desired operating density and temperature, calculate the appropriate operating pressure, and control to that pressure. The independent control of pressure and flow enables the chemist to vary the extracting fluid solvent power by choosing operating pressure and to vary the rate (or efficiency) of extracting fluid throughput by varying the pump flow rate. With the parameters decoupled, the user can extract over the range of both parameters for a selected amount of time, i.e., net amount of extraction fluid. Essentially, all these parameters are now independent: flow rate, pressure, and time. In certain embodiments of the present invention, temperatures of many sections of the flow system are also controlled independently as a fourth type of parameter.

As will be readily appreciated by those of ordinary skill, the present invention provides a significant advance in the development of supercritical fluid chromatography (SFC) by maximizing chromatographic efficiency. Typical prior embodiments of SFC extraction instruments employed fixed restrictors (holes, lengths of capillary tubing, frits, etc.) to effect the necessary pressure drop from operating with supercritical and near-critical carrier fluids (also known as mobile phases). These fixed restrictors typically had diameters on the order of microns. Such fixed restrictors found in the prior art are different from the "stepwise" variable restrictors and actively controlled variable restrictors described herein that can be used to regulate flow in the present invention. In the application of SFC, the exploitation of the parameters of density (pressure), flow rate, and temperature is as important as doing so in supercritical fluid extraction (SFE). With the fixed restrictors, chromatographers were forced to achieve operating pressures by varying the flow rates. This is undesirable, however, since in chromatographic separations, flow rate is an important parameter in separation efficiency. Often the flow rates necessary to achieve high pressures are far too high to be operating at the most efficient chromatographic region, i.e., the minimum of the van Deemter curve. Independent control of pressure (density) and flow rate, as disclosed by the present invention therefore allows the appropriate chromatographic operation.

Figure 3:
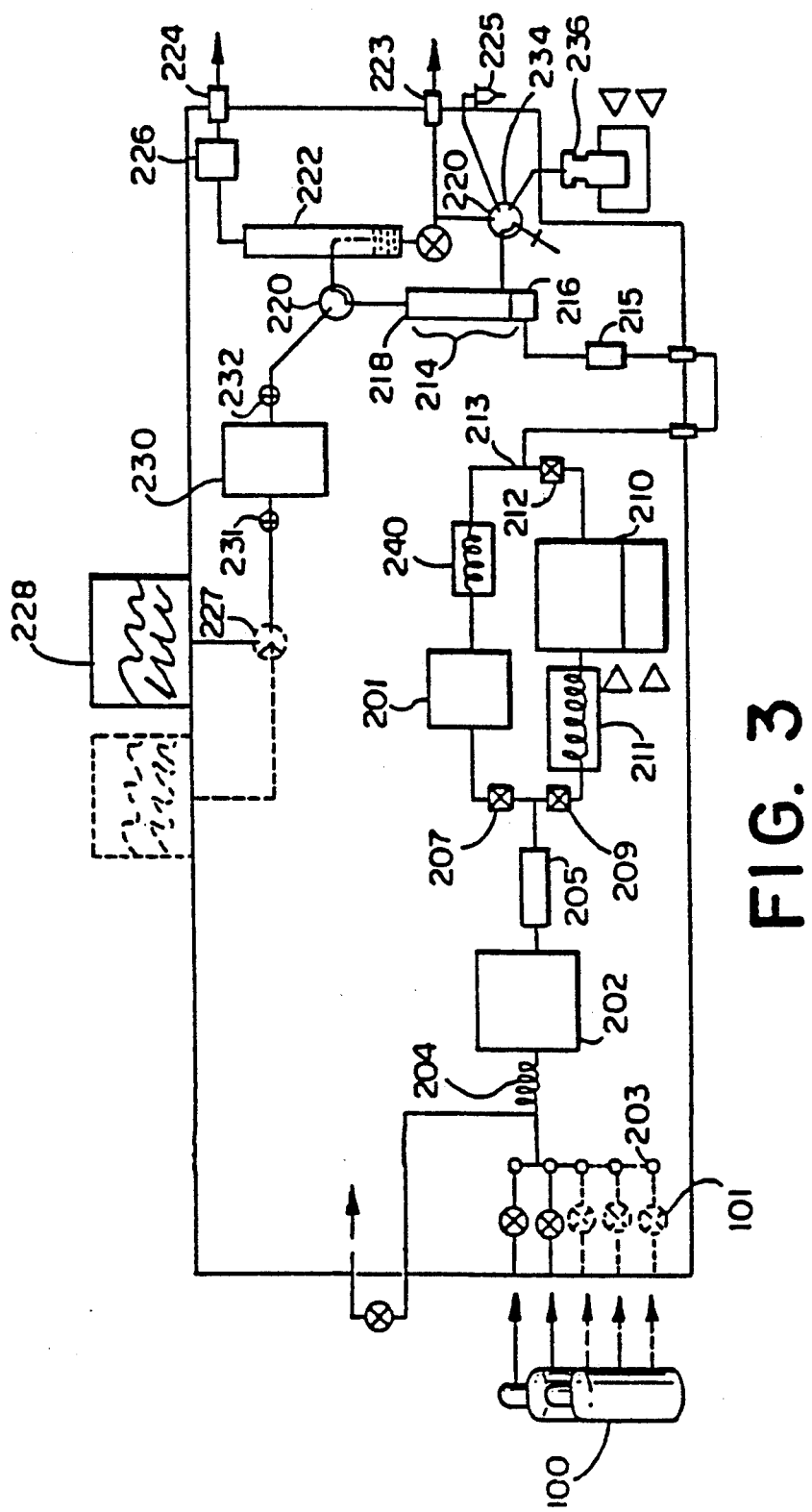
FIG. 3 shows a schematic representation of an embodiment of an extraction instrument made in accordance with the present invention.

Referring now to FIG. 3 a preferred embodiment of the apparatus of present invention for the extraction of components from solids, semi-solids, and small-quantity liquids is provided. The apparatus comprises multiple extraction fluid input ports from gas cylinders 100, each having valving 101 and, in some instances an accompanying check valve 203 located downstream, to provide port selection of multiple-to-one, as desired. A heat exchanger 204 for control of fluid temperature upstream and just prior to injection into the pump 202 may also be included. The solvent then flows through a high pressure pump 202 which can be thermally controlled to give desired fluid compressibility within the pumping chambers. To attenuate the pressure ripple due to pumping of the fluid a pulse damper 205 is provided downstream from the pump 202. The flow is then divided into two sections, referred to as the "bypass" and "chamber" sections. Valving 207,209 is supplied to direct flow to either, both, or neither of the two sections noted above.

The chamber section of the flow system is regulated by the lower valve 209, shown in FIG. 3. A preheater 211 may again be included in this section of the flow system in order to regulate the temperature of the solvent. An additional preheater 240 may also be provided in the bypass section. The fluid then flows into the chamber 210 where extraction takes place. As shown schematically, the chamber 210 of the present invention is preferably actuated between two positions. This actuation permits the chamber 210 to be automated and to include apparatus for automatically creating the high pressure seals necessary between the chamber 210 and the vessel containing the sample. Since the chamber 210 is actuated between the two positions shown, flexible couplings, including tubing for the fluid connections and flexible electronic connections for thermal control and power signals are provided since it is necessary that the apparatus of the present invention supply fluid to an actuated section.

The sample input module contained within the chamber 210 preferably allows a sample to be inserted in the flow stream via the extraction chamber 210, with subsequent achievement of all necessary seals made by the actuation provided. The design of the sample input vessel interface and actuators preferably permits various sizes of cylindrical containers to be accommodated. The sample input module, referred to as a "thimble," preferably is a common vessel in an automated laboratory bench, permitting the same vessel to serve as a sample transport vessel, as a part of an solid phase extraction cartridge, and as a part of a filtering apparatus and to serve other functions.

As pointed out above, the flow system of the present invention may in certain embodiments include a bypass section, controlled by the upper valve 207, shown in FIG. 3. The bypass section routes fluid flow around the extraction chamber section 210 containing the sample to allow equilibration of all controlled setpoints, before sampling of the contents of the solution from the chamber/cylindrical container occurs. The pressure of the fluid delivered by the high pressure pump is measured by a pressure transducer 201, which is illustrated as being located within the bypass section. However, in other embodiments of the present invention, the transducer 201 may be located elsewhere, or one or more additional transducers be included in order to more completely monitor the pressure at various points in the flow system.

Meaningful control of the solvent power of the extracting fluid via pressure/density is achieved using the pressure transducer 201. As will be understood by those of ordinary skill, the design of such a pressure transducer 201 must meet appropriate accuracy and precision specifications. The transducer 201 is preferably mechanically chosen to minimize dead volume to the fluid stream and is placed close to a back pressure regulation subassembly and relatively close to the exit of the chamber 210 in order to minimize pressure drop to both of those sections. Those of ordinary skill will also readily understand that FIG. 3 is thus a schematic of the present invention and the relative placement of the components described is determined by the operating specifications of the system and the performance of the components chosen.

The bypass and extraction chamber flow paths described above are subsequently merged together at a juncture 213 to flow into the nozzle/trap subassembly 214 through the use of appropriate valving and filtering. To minimize the failure of the nozzle/trap subassembly 214 due to particulates, a filter 215 is preferably provided directly upstream of the nozzle/trap subassembly 214. In certain embodiments of the present invention, the nozzle/trap subassembly 214 can be made in accordance with U.S. Pat. No. 5,009,778 referenced above.

The flow is then routed to the subassemblies that make up the sample collection section of the system in which the high pressure fluid comprising pure extraction solvent, mixed extraction solvents, and/or mixtures of extracted components dissolved in the extracting solvent encounters a pressure drop in the nozzle subassembly 216. The pressure drop allows splitting the extracting solvent from dissolved components, since high vapor pressure liquids such as liquid carbon dioxide or subcritical or near-critical mixtures of fluids such as carbon dioxide plus methanol expand upon encountering a pressure drop.

The nozzle subassembly 216 also provides a back pressure regulation function as part of the pressure control loop and a thermal control zone. However, flow control is independent of pressure/density control. As explained above, in a preferred embodiment of the apparatus of the present invention, flow control is provided by a pump 202; however, in other embodiments, also explained above with references to FIGS. 1 and 2, it is possible to use the nozzle 216 for flow control and have the pump 202 control the pressure and density.

For those fluids which remain liquid upon encountering the pressure drop at the nozzle 216, the trap subassembly 218 is operated to vaporize them downstream. The trap subassembly 218 provides a section to baffle the expanding flowing gas stream in which precipitating extracted components are entrained. The trap subassembly 218 may be filled with porous or granular material which is either inert or which has some chemical activity, such as adsorbents, or some chemical functionality, such as stationary or bonded liquid phases. Those of ordinary skill will readily understand that the filling or packing used within the trap subassembly 218 is a parameter which the user may exploit for fractionation.

Fractionating in the region downstream of the extraction chamber 210 in a supercritical fluid extractor made in accordance with the present invention may employ the wealth of stationary phases found to provide specificity in the fields of analytical and preparative scale chromatography (e.g., gas-liquid and gas-solid chromatographies, normal and reversed phase liquid chromatographies, normal and reversed phase thin layer chromatographies, adsorption chromatography, supercritical fluid chromatography, size exclusion chromatography). Thus, in certain embodiments, the apparatus described herein can superimpose chromatographic-like selectivity due to stationary phase interaction on the fractionating capability inherent in a supercritical fluid extraction device for clean-up of samples in the analytical lab.

There are several ways to obtain the above-described "hyphenated" solution. The first is to expand the solution, deposit dissolved components on the trap 218 which is part of the variable nozzle/trap assembly 214. This deposition should occur in as narrow a zone as practical. Next, a mobile phase is passed through the trap 216 to move components through the trap stationary phase material with selectivity as explained above. This can be accomplished, for example, with a liquid so that take-up simulates liquid chromatography. Other embodiments can exploit temperature and a gaseous mobile phase so that migration is more similar to gas chromatography or, in the extreme, thermal desorption. A near-critical or a supercritical fluid is most preferably used as the mobile phase. In the last example, this would permit the introduction of a fraction to a supercritical fluid chromatograph made possible, for example, by arranging the connections to the nozzle/trap subassembly 214 such that the trap 218 is part of a chromatographic sampling system.

Figure 10:
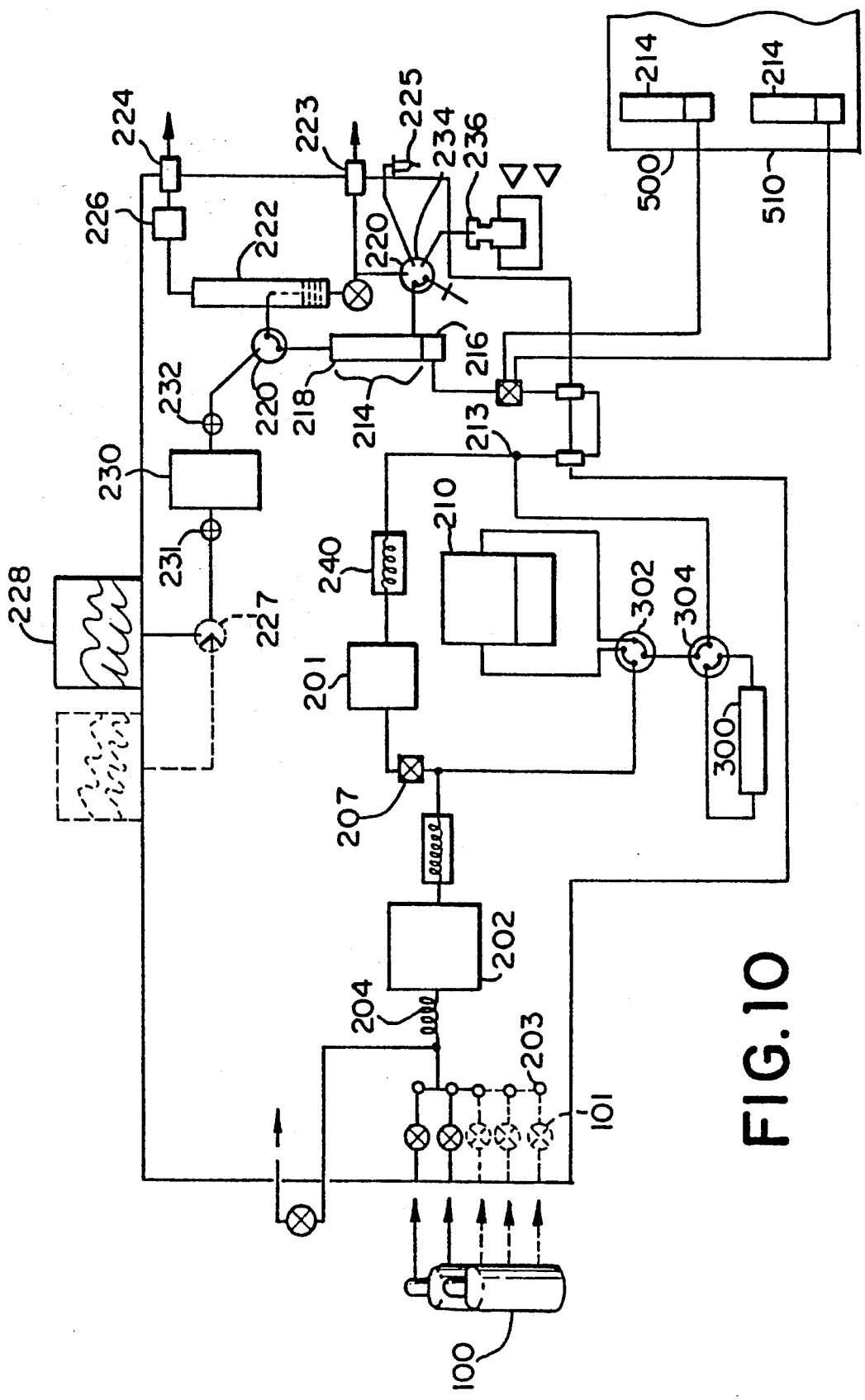
FIG. 10 depicts another embodiment of the apparatus of FIG. 3 including additional enhancements.

Another embodiment, illustrated in FIG. 10 would include a fractionation zone 300 inserted between the sample chamber 210 and the expansion nozzle 216. In this case, selective retention within the fractionation zone 300 of some of the components dissolved in the extraction fluid as it left the sample chamber 210 would alter the group of extractants that were deposited in the expansion occurring in the collection region, i.e., the nozzle/trap subassembly 214. Appropriate valving 302,304, along with thermal and pressure control permit the subsequent removal, possibly in selective steps, of the retained components from the fractionation zone 300—with collection again in the nozzle/trap subassembly 214. Yet another embodiment would include placing a stationary phase within the sample chamber 210 with the sample so that the additional selectivity is superimposed.

Group separations of similar chemical functionality, physical structure or molecular weight are an important application for the hyphenated fractionation embodiments of the present invention described immediately above. Often, fractions obtained from extracts need further processing and it is frequently an analytical chemist's goal to produce groups of compounds with similar structures (e.g., monogalactosyldiglycerides separated from digalactosyldiglycerides, branched hydrocarbons separated from straight chain hydrocarbons, saturated hydrocarbons from unsaturated hydrocarbons, high molecular weight polymers from oligomers and solvents). Several chromatographic studies in the prior art illustrate this need. An early industrial scale study with supercritical fluid separations on stationary phases demonstrated separation based on shape/size: a mixture of n-paraffins and isoparaffins is separated into two groups using a molecular sieve packing as discussed in W. Ecknig and H. J. Polster, *Superkritsche Chromatographie von Paraffin an Molecularsieb, Tell I. Methodishe Grundlagen and Teil II. Chromatographisches Verhalten in Abhangigheit von Druck der mobilen Phase*, Chem. Tech. (Leipzig), 31 (1979), pp. 89 and 245. Another example is the replacement of the industry standard fluorescent indicator adsorption (FIA) analysis set forth in Norris and Rawdon, Anal. Chem. 56 (1984) p. 1767, with the separation of total saturates, olefins, and aromatics from a petroleum product using silica and silver nitrate impregnated silica stationary phases and supercritical fluid mobile phase. Finally, several examples of "Dense Gas Exclusion Chromatography" have been disclosed studying several mixtures and porous silica glass stationary phases. See "Dense Gas Chromatographic Studies," L. Bowman, Ph.D. Dissertation, University of Utah, 1976, Chapter IV. It should be noted that the term "dense gas" is one of several terms used earlier to describe supercritical fluids.

Thus, as seen in FIG. 10, either a gas chromatograph 500 or a liquid chromatograph 510 can be connected via a high pressure valve 502 at a point downstream from the extraction chamber 210 and upstream from the nozzle/trap subassembly 214. Both the gas chromatograph 500 and the liquid chromatograph 510 preferably include a nozzle/trap subassembly 214 as part of each chromatograph 500,510.

In certain embodiments of the present invention, the trap 218 is also an independently controlled thermal zone which may be operated between sub-ambient and heated conditions. For those extraction fluids not vaporized by encountering a pressure drop, the thermal control of the trap subassembly 218 is used to vaporize such fluids as, for example, hexane, or modifiers used to make modifier-carbon dioxide mixtures. Furthermore, subsequent to collection of the extracted components, the temperature of the trap may be increased to a level sufficient to thermally desorb collected components, which would be transported by a gas-like mobile phase at appropriate conditions of pressure, flow rate and identity to analytical instruments, such as gas chromatographs, supercritical fluid chromatographs and liquid chromatographs.

The apparatus of the present invention as illustrated in FIG. 3 preferably includes one or more actuated diverter valves 220 which have positions allowing direction of exhausting vapors to vent/waste positions during extraction, and to direct rinsing solutions to collection hardware of various sizes or to vent/waste during rinse sequences. The actuated diverter valves 220 preferably perform valving actions while having minimal dead volume. Valving is also provided to direct the rinse fluid streams or exhausting extraction fluids to different destinations. A first destination, for example, is a splitter column 222 which ends in both a liquid waste stream 223 and a gaseous vent 224. A second destination is a remote port 225. Preferably, the splitter column 222 is controlled at low temperatures and uses demisting components to separate liquid modifiers from the base vaporized extracting fluid or to collect liquid solvents.

As also seen in FIG. 3 flow transducer 226 or rotameter is preferably connected to the top of the splitter column 222. The splitter column 222 is also connected to the actuated diverter valve 220, which comprises ports by which rinse solvents are supplied. A valve 227 (or multiple valves) is supplied to select one or more rinse solvent streams from one or more rinse solvent reservoirs 228, which supply the rinse solvent pump 230, which can withstand system pressure. The rinse solvent pump 230 preferably has a variable dispense rate appropriate for liquid-chromatographic type zone movement and can be directed to supply user-selected collection volumes at the chosen destination. The rinse solvent pump 230 may be configured with an active inlet valve 231 or an active outlet valve 232 for more reliable operation. These valves may also be typical check valves or switching valves.

Thus, under selected conditions, rinse solvent is directed through the rinse solvent pump 230 and the diverter valve 220 into the trap subassembly 218 to dissolve precipitated components and move them to the fraction collection destination chosen by the user. The direction of the rinse solvent through the trap 218 can be foreflushed or backflushed relative to the flow of the extraction fluid during the extraction step. FIG. 3 illustrates a backflushed system, although foreflushed is also a preferred embodiment of the present invention. The present invention therefore permits the removal of deposited components by either back flushing or foreflushing using a second fluid, e.g., typical liquids such as organic solvent systems, acids, bases, aqueous solvent systems; sub-, near- and supercritical fluids including mixtures; or by thermal deposition into a gas stream. As explained more fully below, other embodiments of the present invention permit these rinsing steps to affect one or more sections of the apparatus in addition to the nozzle/trap subassembly 214.

The trap subassembly 218, is connected to liquid waste port 223, remote port 225 and automatic liquid sample vials 236, preferably in a queue, by an actuated valve 234 that may be similar to the diverter valve 220 described above. The actuated valve 234 supplies a sample vial 236, which is preferably actuated to move up and down in order to facilitate automation, as explained above with reference to the extraction chamber 210. Thus, in a preferred embodiment, the apparatus of the present invention also comprises a queue of sample vials 236 which can collect multiple fractions in sample vials such as the autosampler vials which are typically used in gas and liquid chromatographs. There are numerous variations by which a supercritical fluid extraction device made in accordance with the present invention may be operated to provide optimal recovery, while minimizing the down-time encountered while maintenance or servicing.

Figure 4:
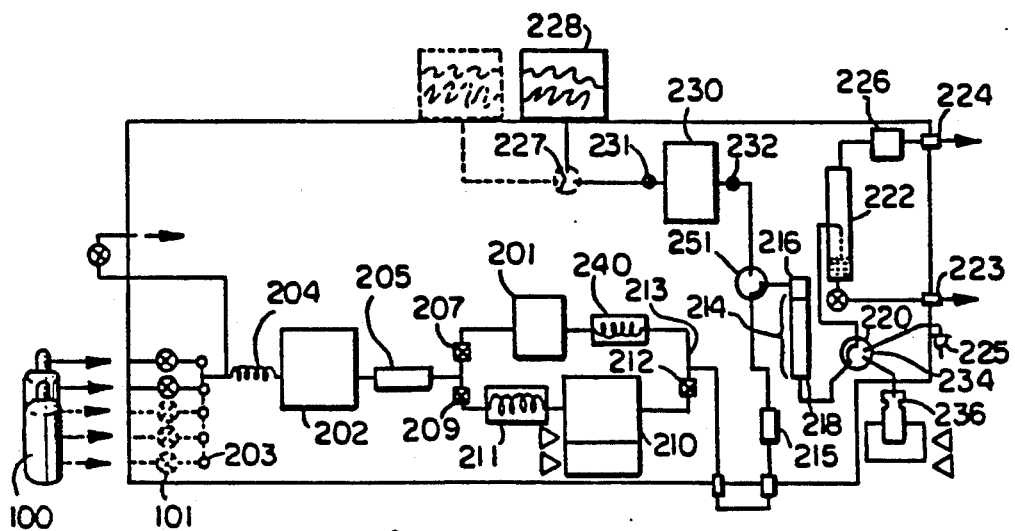
FIG. 4 is a schematic representation, similar to FIG. 3, which depicts an embodiment of the present invention including a rinsing section adapted to minimize occlusion.
Figure 5:
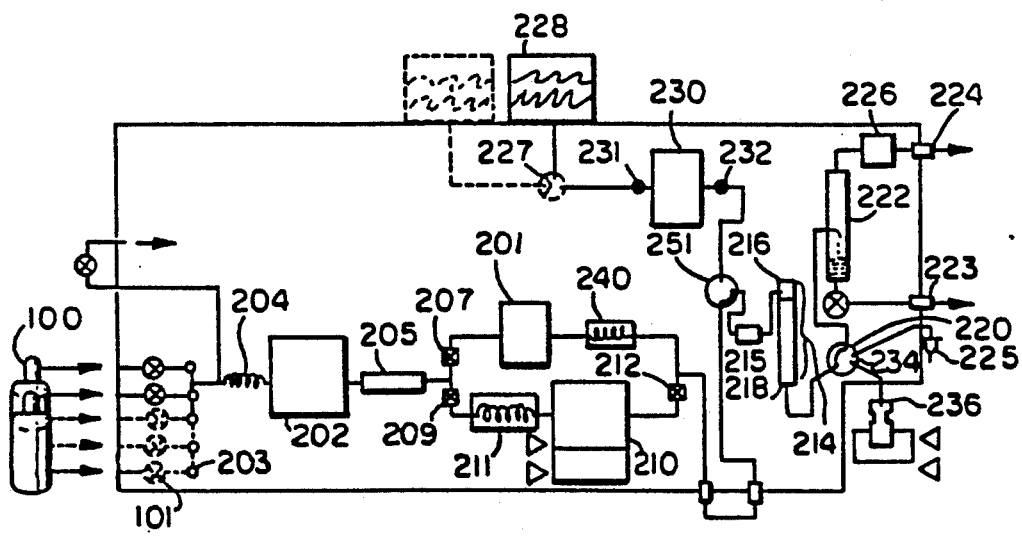
FIG. 5 is a preferred embodiment of the rinse section shown in FIG. 4 adapted to minimize occlusion.

As discussed above with reference to FIG. 3, in certain embodiments of the apparatus of the present invention, the flow is divided into two sections, referred to as the "bypass" and the "chamber" sections. Accordingly, valves 207,209 and other flow control apparatus are provided to direct flow to either, both or neither of the bypass and chamber sections. The bypass section routes fluid flow around the extraction chamber 210 which contains a sample disposed within the sample input module to allow equilibration of all the controlled set points with the flow before initiating the sampling of the contents of the solution from within the extraction chamber 210. The bypass and chamber section flow paths are preferably merged at a juncture 213 and subsequently flow into the nozzle/trap subassembly 214 through the use of appropriate valves and filters. The present invention also provides other flow control apparatus to isolate the bulk of the high pressure flow path from the low pressure rinse section. Filtering apparatus 215 is preferably provided upstream of the nozzle/trap subassembly 214 to minimize failure in the nozzle subassembly 216 due to the accumulation of particulates. Referring to FIGS. 4 and 5, such valves 251 may also be incorporated as shown in these embodiments to route flow through a filter 215 and isolate the bulk of the high pressure flow path from the low pressure rinse section.

In certain embodiments of the present invention, the valves 207,209,212 and the pressure isolation valving 251 noted above (used to isolate the high pressure flow path from the low pressure rinse section) permit the apparatus of the present invention to be configured and operated to overcome problems frequently encountered during supercritical fluid extraction. Such problems include the occlusion of one or more of the fluid control components of the extraction instrument between the sample containment section and the region directly downstream from the restrictors used to maintain system pressure by providing a pressure drop using, e.g., a nozzle 216. The occlusion occurs as a result of the precipitation of dissolved components in the flow stream, the extrusion of melted matrix or matrix components into the flow stream, particulates from the sample that are too small to be captured in filtering devices 215, or the erosion of particles from the apparatus itself, such as metal filings and polymeric particulates from sealing components, and the subsequent accumulation of such particulate matter.

In the rinsing methods of the present invention, fluid is delivered either at an appropriate pressure and flow rate to dislodge and transport insoluble particulate matter through the throat section to the expansion region downstream, or at an appropriate pressure, flow rate and solvent power to solubilize or dissolve deposited, precipitated or adsorbed components and transport the resulting solution through the throat of the nozzle 216 to an expansion region such as the trap 218. Finally, the rinsing method concludes with the step of restoring the configuration of the system so that the rinse solvent supply is isolated from the high pressure side of the nozzle 216.

Thus, a preferred embodiment of the present invention provides a device which permits rinsing the nozzle throat to prevent the accumulation of particulate matter. First, the rinse solvent supply 228 is merged with the inlet line to the nozzle 216. This merger will occur on the high pressure side of the apparatus during pressurized operation. Preferably, the merger is accomplished by activating a valve 251, as shown in FIGS. 4-5, and may occur immediately upstream of the nozzle inlet, or alternately, at any other point in the instrument which permits the solvent to eventually flow to the nozzle inlet. Thus, the merger may be accomplished at a valve upstream from the pump 202 and the heat exchanger 204. Certain embodiments of the present invention may also include means for varying the size of the throat section of the nozzle 216. This would most likely be implemented where the nozzle 216 comprises a variable annular orifice nozzle that is most preferably provided with electronic control of the orifice size, as discussed above.

Referring now to FIG. 4, there is illustrated another preferred embodiment of a supercritical fluid extractor made in accordance with the present invention and comprising apparatus for rinsing the throat of the nozzle 216. As illustrated, a valve 251 which isolates the rinse solvent reservoir 228 from the nozzle 216 is placed immediately upstream of the nozzle 216, permitting the flow to be controlled and rinse the nozzle 216 when desired.

Alternately, apparatus for rinsing the throat of the nozzle 216 may be constructed as illustrated in FIG. 5. In this embodiment, the valve 251 which isolates the rinse solvent reservoir 228 from the nozzle 216 is placed upstream of the filter device 215, described above which is upstream of the nozzle 216. The advantage of this embodiment is that any soluble material deposited on the filter device 215 and the valve 251, as well as from other components, such as valve conduits, fittings, the inner surfaces of tubing, the preexpansion region of the nozzle 216 and other portions of the nozzle/trap assembly 214 is removed by the rinse process. A further advantage is that the filter 215 protects the nozzle 216 from particulates which may be present in the rinse solvent and wear particles that are typically encountered in actuating valves. Thus, the embodiment depicted in FIG. 5 cleans and keeps the nozzle 216 free of both the particulates and deposited soluble material. Essentially, the apparatus depicted provides on-going maintenance which is transparent to the user. This embodiment of the apparatus minimizes instrument failures and the need for user intervention to address failures which typically occur due to blockage in existing extraction systems.

Figure 6:
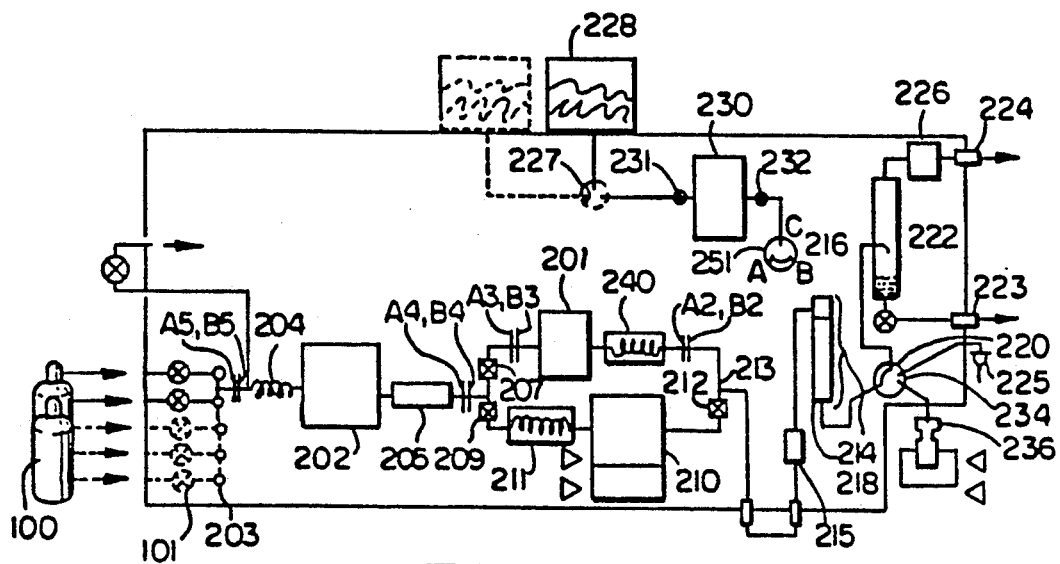
FIG. 6 illustrates a further embodiment of the present invention as shown in FIGS. 4-5 that includes a rinse section to minimize occlusion and valving to permit rinsing.

FIG. 6 illustrates another embodiment of the apparatus of the present invention adapted for rinsing the throat of the nozzle 216. In this embodiment, the valve 251 which isolates the rinse solvent reservoir 228 from the nozzle 216 is slightly different from that of FIGS. 4–5. The valve 251 is placed at any point upstream of a filter device 215, which is upstream of the nozzle 216 and in a flow path configuration which does not pass through the sample. In this embodiment, the apparatus makes use of the valve 212 positioned near the juncture 213 of the bypass and chamber section flow paths to control the flow, particularly to prevent or allow flow of liquid solvent in the chamber 210. In the embodiment illustrated in FIG. 6 the valve 251 most preferably has at least three ports, designated A,B,C. As illustrated, port "C" is connected to the rinse solvent pump 230. Ports "A" and "B" provide flow continuity during extraction by isolating the rinse solvent pump 230 from the system. However, during rinsing steps, ports "A" and "B" are resident on valve 251 and connected to one or more of the other "A" and "B" ports noted on FIG. 6. For example, ports "A2" and "B2" are disposed downstream of the bypass pressure transducer 201; ports "A3" and "B3" are disposed upstream of the bypass preheater 240; ports "A4" and "B4" are disposed immediately downstream of the pulse damper 205; and ports "A5" and "B5" are disposed immediately downstream of the extraction fluid input check valves 203. In order to better illustrate the present invention, the connections between the pairs of ports "A" and "B" are not shown. These or other points of connection may be made, as will be understood by those of ordinary skill, to provide various points where solvent from the solvent reservoir 228 may be introduced to rinse the apparatus. In addition to the advantages set forth above in relation to the apparatus of FIG. 5, the embodiment illustrated in FIG. 6 has the further advantage of providing more extensive cleaning, i.e., more of the apparatus is flushed with each rinse cycle.

Figure 7:
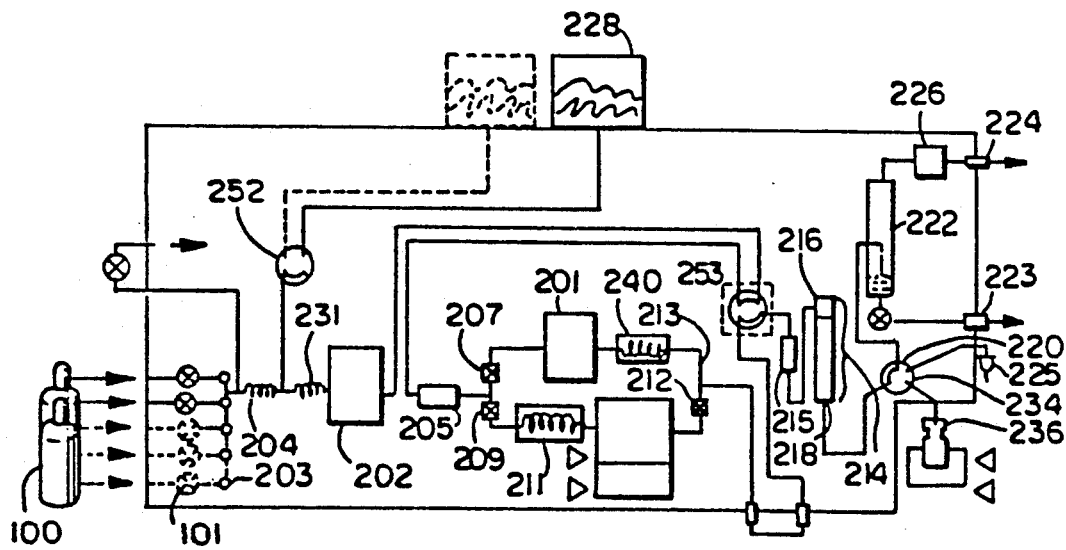
FIG. 7 is another embodiment of apparatus including a rinse section adapted to minimize occlusion and that uses a single pump for both extraction and rinse fluids.

FIG. 7 illustrates another embodiment of the apparatus of the present invention that is adapted for rinsing the throat of the nozzle 216 in accordance with the present invention. A first rinsing valve 253 and a second rinsing valve 252 are provided which isolate the rinse solvent reservoir 228 from the extraction solvent supply while using the high pressure pump 202 to deliver appropriate fluids at appropriate times during the preparation method.

Figure 7A:
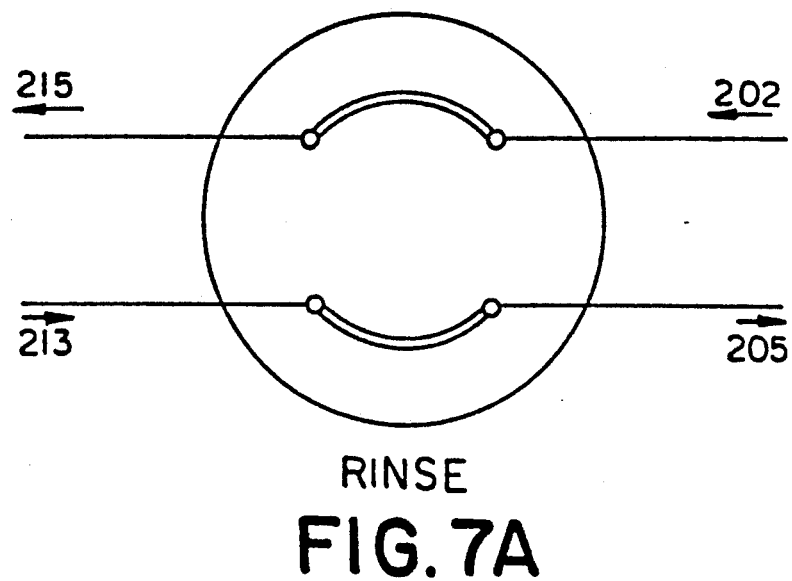
FIGS. 7A and 7B schematically depict the position of the connections in a valve used in the embodiment of FIG. 7.
Figure 7B:
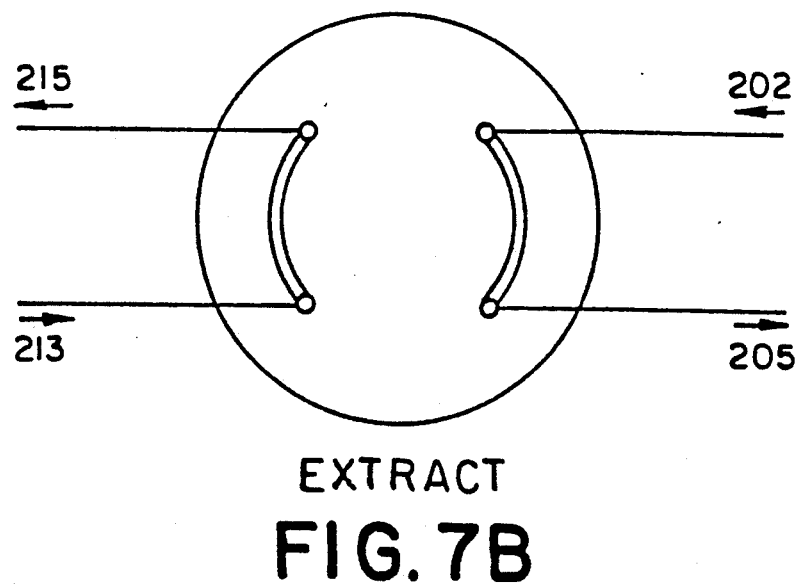

Referring to FIGS. 7A–7B, the operative connections of the first rinsing valve 253 during both a rinse step and an extraction step are illustrated. During a rinse step, illustrated in FIG. 7A, the fluid delivered by the pump 202 is directed to the filter 215 and subsequently into the nozzle 216, performing the rinsing thereof. The other flow path isolates the rest of the extraction instrument from the juncture 213 between the chamber and bypass flow paths to the entry side of the pulse damper 205. During an extraction step, the position of the first rinsing valve 253 is preferably changed to that illustrated in FIG. 7B. As shown, the high pressure fluid delivered by the pump 202 is delivered directly downstream to the pulse damper 205. The other flow path isolates the flow between the juncture 213 of the chamber and bypass flow paths and the filter 215, which is upstream of the nozzle 216.

Thus, in the embodiment of FIG. 7, the need for a separate pumping apparatus associated with the flow of solvent from the solvent reservoir 228 is eliminated. The first rinsing valve 253 may be inserted anywhere within the flow stream, as was the case with the embodiments described above with reference to FIGS. 4–6. In addition to the advantages set forth above in relation to the apparatus of FIGS. 5–6, the embodiment illustrated in FIG. 7 has the further advantage that it uses a single pump 202 to deliver both fluids at pressures, flow rates and compositions appropriate to the selected preparation method.

A further aspect of the present invention is the provision in some embodiments of methods and apparatus whereby a solution of extract is diluted with extracting solvent in order to reduce the concentration of the solvated components. The solution obtained thereby is more robust to changes in flow stream conditions, e.g., passage through conduits of varying cross-section, temperature gradients and pressure drops, such that precipitation or adsorption or both of the extracted components along the flow path is minimized upstream of the nozzle region. Dilution in accordance with the present invention is accomplished by merging a flow stream of pure extraction fluid, which is supplied through the bypass section along with the flow stream of the extract solution, i.e., the extract plus the extraction fluid. In certain embodiments of the present invention, the stream of pure extraction fluid may be a multi-component solvent mixture. The merger of the streams occurs before or at the same time as the streams flow from the extraction chamber 210 to the nozzle 216, and the fluid streams preferably remain merged throughout the remainder of the process.

Accordingly, referring again to FIG. 3, apparatus for decreasing the concentration of an extraction solution within a supercritical fluid extraction apparatus is preferably comprised of a valve 207 to admit flow to the bypass section and a valve 209 to admit flow to the region within the extraction chamber 210. A junction 213 is also provided for merging the two flow paths. In accordance with this aspect of the present invention, the apparatus in FIG. 3 is not altered except to alter the degree to which the flow paths through the instrument are controlled. The appropriate degree of dilution is obtained by providing a control means for controlling the two valves 207,209, i.e., opening, closing and varying the flow rate through the valves 207,209. As readily appreciated by those of ordinary skill, such control means may comprise software controls, firmware controls or hard wired electronic drives. In certain embodiments, a user interface may also be provided to permit the user to select the appropriate degree of dilution. Finally, the extraction chamber apparatus 210 also preferably includes calculating means for determining the actual chamber volumes swept and transmit information to the user regarding the actual extent of the contact between the sample and the extracting fluid.

Figure 8:
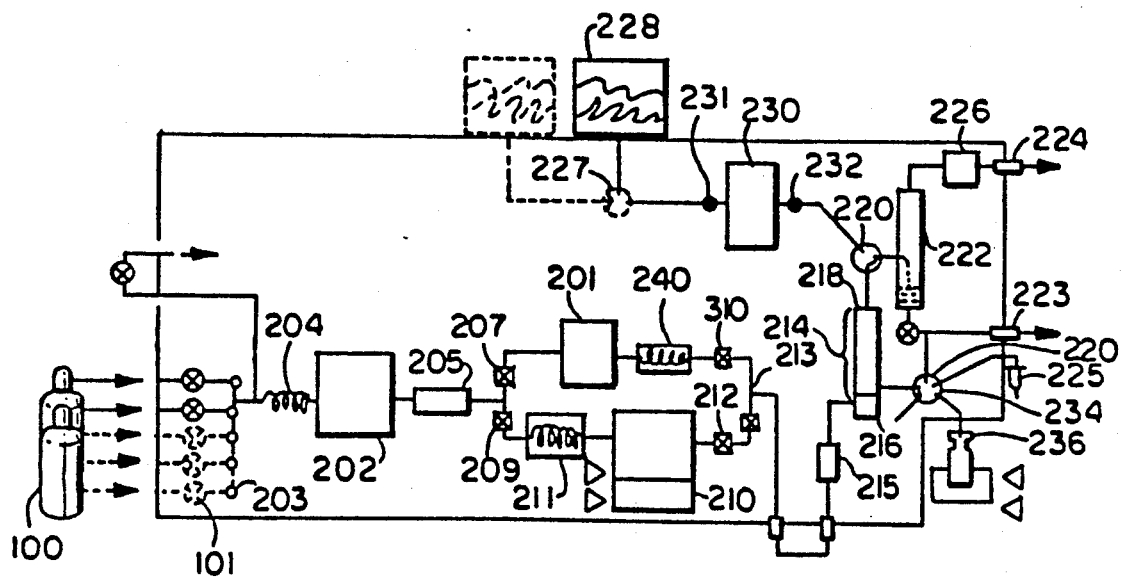
FIG. 8 illustrates an embodiment of the present invention providing means for diluting the extraction fluid.

FIG. 8 depicts an alternate apparatus for decreasing the concentration of an extraction solution within the extraction section of a supercritical fluid extractor. As illustrated, a valve 207 admits flow to the bypass section and another valve 209 admits flow to the sample containment region. A junction 213 is provided to merge the flow of these two sections. In the embodiment of FIG. 8, however, a restriction means 310 is placed in the bypass flow path. Additionally, in certain embodiments, a further restriction means 320 is placed in the extraction chamber flow path. The degree to which the restriction means 310,320 restrict the flow is chosen to give the appropriate apportionment of extraction fluid between the two flow paths when both the bypass and extraction section valves 207,209 remain open. The apparatus also preferably comprises control means to operate in the "dilution mode" by having both valves 207,209 open during the extraction portion of the method of the present invention or to operate in the "undiluted mode" by selectively operating the valves 207,209 to permit timed operation. As described above, the control means may be comprised of software controls, firmware controls or hard wired electronic drives. As described above with reference to FIG. 3, the preferred embodiment of the present invention illustrated in FIG. 8 also includes means for calculating the actual chamber volumes swept.

Figure 9:
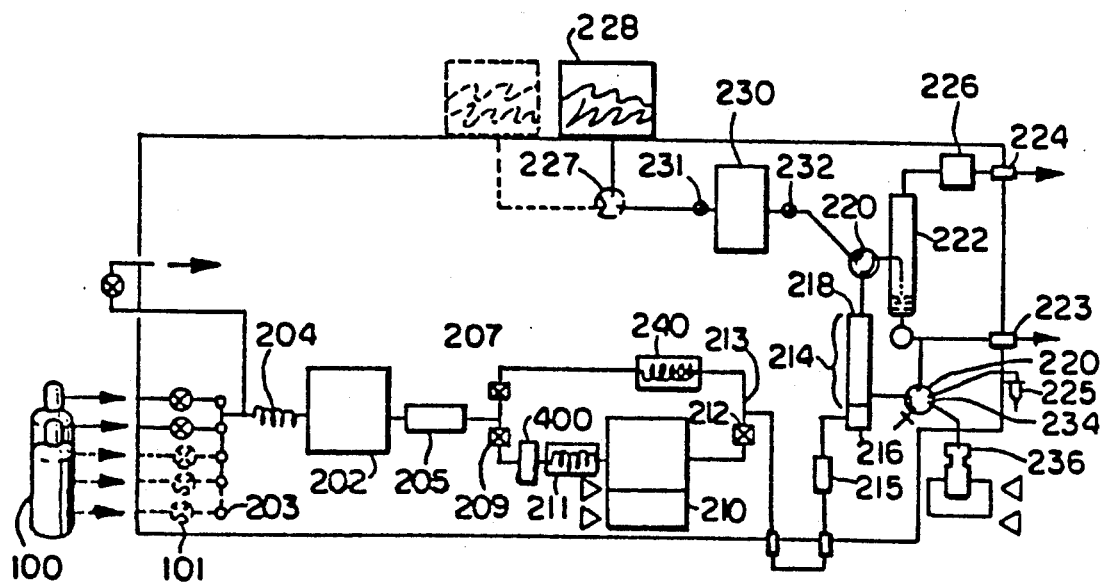
FIG. 9 is an alternate embodiment of the apparatus depicted in FIG. 8.

A further embodiment of apparatus for decreasing the concentration of an extraction fluid solution is depicted in FIG. 9. Preferably, valves 207,209 to control flow to the bypass and extraction sections respectively and a junction 213 for joining the flow paths are again provided. A mass flow sensor 400 is placed directly upstream of the sample containment area 210. As part of the bypass valve 207 a means for controlling flow adjusts the degree to which the valve 207 restricts the flow, is located in the bypass section, and varies the flow through the sample containment section 210. Finally, calculating means for calculating and indicating the actual chamber volumes swept by integrating the instantaneous mass flow rate over time (not illustrated) are also preferably provided as part of the operation and control system of the extractor instrument.

One of ordinary skill will realize that although the methods and apparatus described above have distinct application to solve a number of problems, it is further desirable to combine the features of the methods and apparatus described to achieve other improved results. Accordingly, for example, the present invention provides a method for diluting a solution of extract in an extracting solvent in order to reduce the concentration of the solvated components, with the attendant advantages set forth above, combined with a method for rinsing through the nozzle throat. A combined method in accordance with the present invention entails selecting the degree of dilution to be employed and providing information describing the resulting degree of sample contact with the extracting fluid, e.g., swept volume; the other set point parameter values are then input or chosen. An extraction process is then executed, followed by a rinsing method in accordance with the present invention. Subsequent extraction and rinse steps are repeated as required and, in certain embodiments, further dilution may also be implemented for each subsequent extraction step.

While the primary form of sample which the apparatus of the present invention accepts comprise solid samples, it is possible to introduce small quantities (i.e., microliter to milliliters in volume) of liquid by distributing the liquid upon solid supports such as filter paper, adsorbents, or powders. Similarly, semi-solids such as fats and creams can be input.

In other embodiments of the present invention, it may be desirable to include one or more further nozzle/trap subassemblies additional to the nozzle/trap subassembly 214 described above with reference to FIG. 3. As seen in FIG. 10 and explained above, such additional nozzle/trap assemblies 214 would either be incorporated into the apparatus of the present invention or resident on other instruments coupled thereto. In some cases, an additional nozzle 216 may be the only additional subassembly. In other embodiments, the nozzle and/or trap subassemblies resident on other instruments may be substituted entirely for those preferably provided as a part of an extractor made in accordance with the present invention. Additionally, the hardware of the nozzle/trap subassemblies 214 may be specialized to assume functions within the apparatus of the present invention or the instruments on which they are resident, examples include: injection ports on gas chromatographs, precolumn or heart-cutting on liquid chromatographs and supercritical fluid chromatographs. As known to those of ordinary skill, heart cutting is a technique used in liquid chromatography for selectively introducing parts of a complex sample presented to the liquid chromatograph to the analytical column.

Another modification to the apparatus of the present invention is the inclusion of means for hooking up additional connections between the remote port 225 and/or the trap exits 223,224 and other analytical instruments—e.g., particularly liquid chromatographs, UV/VIS spectrophotometers, and liquid samplers—such that the fraction rinsed from the trap 218 can be directed to those instruments for further manipulation and subsequent analysis.

Similarly, the apparatus disclosed in FIG. 3 can be modified to provide sampling of the fluid solution leaving the extraction chamber 210 prior to recovery of solutes in the nozzle/trap subassembly 214 or prior to being directed to other instruments such as through the sections 530 or the fractionation zone 300 shown in FIG. 10. For example, the sampled stream, possibly at high pressure, may be directed to a UV/VIS spectrophotometer or through sampling valves on a variety of other analytical instruments such as liquid chromatographs, supercritical fluid chromatographs, and gas chromatographs, in a manner similar to that illustrated in FIG. 10 where a fractionation zone 300 is added. The fractionation zone 300 is a component of a "heart cutting" implementation of the present invention.

As set forth above with reference to FIG. 3, the trap 218 may be filled with a packing material. However, alternate embodiments of the apparatus of the present invention may include additional regions containing some chemically active packing material (e.g., typical liquid chromatographic column packing materials, adsorbents, or other porous material) and additional thermal zone control and hardware and additional valving to control the fluid direction to such regions. The addition of such apparatus permits the apparatus to be used to provide fractionation of the mixture of the solution leaving the extraction chamber 210 containing the sample before that solution encounters the nozzle and/or trap subassembly 214. Flow through the chamber and bypass regions discussed above is coordinated along with thermal zone operation to deposit sample material in the fractionation zone and then selectively remove components from that zone. The components are collected in any of the apparatus configurations outlined above.

It is known in the areas of analytical scale chromatography and preparative scale chromatography to choose stationary phases to have selective interaction with various molecules which come into contact with the stationary phase. When the motion of a mobile phase can move molecules relative to a stationary phase, the selective interaction can result in separations of different compounds. Typical mobile phases are liquids, gases, and supercritical fluids. Stationary phases can be supported as films or layers on a surface (e.g., thin layer chromatography, open tubular or capillary column chromatography) or on particles with which fluids can come in contact. Thus, even the surfaces may be considered to be the stationary phase, possibly having been modified for chemical activity, functionality, or size selectivity, e.g., bonded phase chemistry, adsorption chemistry, chiral interactions. It is also known to exploit the physical dimensions of the stationary phase to maximize selectivities, for example with respect to the chosen mobile phase characteristics (van Deemter and Golay equations), or with respect to the diffusion time through liquid layers and within pores, or with respect to the spatial geometry (overall size and shape) of the migrating compounds. The last example is more relevant to particles making up the stationary phase. In some cases, the selectivity may be extreme, some or all of the species migrating with a bulk mobile or carrier phase are substantially irreversibly removed from the mobile phase and retained by the stationary phases.

In terms of the present invention any of the physical or chemical characteristics which contribute to some degree of selectivity of movement among various migrating species exposed to that stationary phase media are defined as "chemically active."

In other embodiments of the present invention the queue of sample collection vessels 236 described above may be supplemented with additional fraction queues which provide for any of the following functions: collection of more autosampler vials, reading and/or writing of labels on the autosampler vials (bar code labels), further fractionation of the components in the fraction solution by solid phase extraction or other typical wet chemical manipulations, and reactions encountered in analytical laboratories to obtain solutions appropriate for the selected analytical method including quantitation.

Also, automated apparatus can be provided for placing the extraction containers in the extraction chamber 210, removing extraction containers from the chamber 210, replacing the extraction containers in a queue/storage area. Reading and writing labels on the extraction containers may also be provided in such embodiments.

In certain embodiments the pump 202 may be modified by providing a pump which is capable of operation for isocratic, binary or ternary solvent delivery to the extraction instrument to blend fluids and fluid mixtures, particularly those which are ordinarily liquid at ambient conditions. The base extracting fluid is coupled via appropriate tubing and valving and coordinated actuation is provided via a workstation or other computer-based controller which can issue commands to the solvent valves and pump. Thus in certain embodiments, the addition of additional pumping channels to blend fluids and fluid mixtures (particularly those which are ordinarily liquid at ambient conditions) with the base extracting fluid to form multicomponent extracting solvents may be accomplished by incorporating further pumps and valving within the extractor instrument to achieve a mixture for the extracting fluid.

Most preferably, valves are provided to select the rinse solvent stream and to supply the rinse solvent pump 230. As described above, the rinse solvent pump 230 can withstand system pressure and has a variable dispense rate appropriate for liquid-chromatographic type zone movement. Valving is provided to direct fluid to supply user-selected collection volumes to chosen destinations.

Finally, as will be understood by those of ordinary skill in the design of such systems, the instrument of the present invention can be coupled with other instruments and techniques in a manner referred to above as hyphenation. Examples of hyphenation which are contemplated by the present invention and set forth above are: high pressure solid phase extraction coupled with supercritical fluid extraction of samples; solid phase extraction as a precursor to supercritical fluid extraction; low pressure fractionation in some embodiments as refined as solid phase extraction on the extract collection trap 218 after the supercritical fluid extraction of the sample; moderate to high pressure fractionation with gases, liquids or supercritical fluids in some embodiments as refined as solid phase extraction on the extract collection trap 218 after the supercritical fluid extraction of the sample with the effluent directed to analytical instruments; thermal desorption of the extract collection trap 218 after the supercritical fluid extraction of the sample with the effluent directed through additional valving to analytical instruments; rinse solvent interface (i.e., the reconstitution solvent) to other instruments; high pressure stream sampling between the chamber 210 containing the sample and the sample collection subassembly 214 (the nozzle 216 which also functions as the pressure control mechanism, and trap 218), so that other devices can monitor or take samples from the high pressure stream; high pressure fractionation in a fractionating region placed between the chamber 210 containing the sample collection subassembly 214; merging the high pressure fractionation with the stream sampling function to analytical instruments with stream sampling function to provide "heart cutting" to analytical instruments; use of multiple sample collection subassemblies; use of a command set which has the features of (a) providing concatenation with other commands from the user to other destinations so that sequences from the extractor instrument can be coordinated with other sequences and (b) primitive commands from which sequences could be built.

It is contemplated that the present invention may be utilized in conjunction with other analytical instruments as shown in the embodiment discussed above with reference to FIG. 10, some of which may include a nozzle and or trap section as described above with relation to the present invention. Such analytical instruments include gas chromatographs, liquid chromatographs, and supercritical fluid chromatographs. Additionally, the present invention may also comprise a fractionation zone 300 for fractionating the extract from the sample. Such a fractionation zone 300 will utilize valving and thermal control means associated with the extraction chamber section 210 and the nozzle 216.

The engineering of the instrument of the present invention applies an understanding of the important parameters and limitations in various areas: supercritical fluids, (supersonic) expansion of fluids, collection/reconstitution of extract, pumping of compressible fluids, setpoint control. As set forth above, the system utilizes a fluid compressibility algorithm for pumping the solvent and utilizes a pressure-volume-temperature algorithm allowing density to be input as the relevant parameter for solvent power (vs. pressure) while providing for decoupled flow and pressure/density control. Preferably, the system permits bypass and/or dilution mode flow to occur. In certain embodiments, extraction solvent fluid composition selection is provided by multiple inputs; in other embodiments extraction fluid composition selection is provided by additional pumping channels. In the embodiment described above which incorporated appropriate valving and controlling software both static extraction and dynamic flow extraction can be achieved. The design of the present invention also provides multiple zone thermal/pressure control to specifications which were based on understanding the impact of these parameters upon density control, particularly for the critical, near-critical and supercritical regions.

The present invention also provides methods for the incorporation of a density/pressure/temperature algorithm into a user interface for setpoint entry and subsequent parameter control. This aspect of the present invention allows the operator to input density as a parameter to instrumentation which uses conventional pressure transducers as part of the electronic control loop to maintain pressure (and, hence, density) at a user-specified temperature. As explained above, at this time, no density transducers are appropriate for general instrumentation for an electronic control loop to control density directly, but could be incorporated into the present invention.

The present invention also provides a method for operating a supercritical fluid extraction system having an electronic pressure control system along with a thermal control systems by which a user can input a desired density to maintain setpoint density without having to regulate the flow rate of the extracting fluid to achieve the density setpoint. First, the operating density and zone temperatures are input via a user interface. The setpoint density is then rounded to a value which is distinguishable as a setpoint given the control capability of the thermal and pressure control loops at the given region of the equation of state. Next, the system calculates the corresponding operating pressure and notifies the user if the combination of the density and temperature setpoints results in pressures outside the operating region of the instrument. The system will then display the corresponding operating pressure to the user so all parameters are visible. Finally, pressure and temperature setpoints are transmitted to the appropriate control loops to maintain density during the extraction or other cycle.

The methods disclosed provide a means to allow the operator to focus on the more significant parameter of density in selecting the parameter setpoints for instrument operation of a supercritical fluid extractor. The operator thus avoids having to use look-up tables, necessarily requiring interpolation among entries for those densities at temperatures and pressures not represented in the table. In operation, the system provides feedback to the user immediately when a specified density cannot be reached due to exceeding the operating boundaries of the interactive parameters—e.g., if some high density and high temperature combinations exceed possible delivery pressure.

Thus, the present invention avoids the user's inputting a parameter (pressure) whose non-linear relationship to solvency is not intuitive and changes significantly depending upon the chosen isotherm when solvency (solvent power) is the key parameter in the instrument. The importance of density as a parameter is instead instilled in new users as well as the discipline of using it.

Based on the equation of state of a particular substance, a control program is created to allow the input of density, with the subsequent calculation of the corresponding pressure at a given temperature. Such a program is a more automated approach to a look-up table, as well as a tool to explore design margins and specifications (temperature and pressure ripples impacting resultant density).

Not only does the present invention encourage the use of density as a more nearly directly proportional solvent power parameter, but also it indirectly prompts users to utilize more conservative setpoint values of pressure, thus leading to longer equipment lifetimes. This last point arises from the "S" shape of isotherms in which, at higher densities, very large increases in pressure result in very small corresponding increments in density.

Although certain embodiments of the present invention have been set forth with particularity, the present invention is not limited to the embodiments disclosed. Accordingly, reference should be made to the appended claims in order to ascertain the scope of the present invention.

What in claimed in:

1. A method of extracting a component from a sample using fluid flow system apparatus comprising control apparatus, at least one element having a variable and controllable flow restriction and a sample container section, comprising the steps of:

inserting the sample into the sample container section;
   inputting temperature, pressure, flow rate and extraction time setpoints into control apparatus;
   providing pressurized fluid;
   directing the fluid to a pump which injects the fluid into the flow system apparatus as a supercritical fluid at the input flow rate setpoint;
   sensing system pressure as fluid is pumped into the system;
   controlling the variable flow restriction to achieve and to maintain the setpoint pressure and achieve a degree of decoupling of flow and pressure;
   directing fluid through the sample at the setpoint flow rate; and
   directing fluid mixture leaving the sample container section to an expansion nozzle section and flowing extraction fluid into a trap.

2. The method of claim 1, wherein the step of directing a fluid mixture through an expansion nozzle section comprises flowing the extraction fluid directly into a trap.

3. The method of claim 2, further comprising the step of sampling the fluid solution leaving sample container section prior to the step of directing the extraction fluid into the trap.

4. The method of claim 1, wherein the step of controlling the variable flow restriction comprises selecting a predetermined orifice opening size and adjusting the flow restriction to the predetermined opening size.

5. The method of claim 4, wherein the step of controlling said variable flow restriction comprises opening and closing a variable orifice.

6. The method of claim 1 further comprising the steps of rinsing the expansion nozzle by connecting a source of rinse solvent to the expansion nozzle section; and connecting the expansion nozzle section tot he fluid flow system apparatus, whereby the rinse solvent supply is isolated from the expansion nozzle section.

7. The method of claim 1, further comprising the step of directing the extraction fluid through a fractionation bed means for retaining chemically active packing material.

* * * * *